United States Patent [19]

Yamazoe et al.

[11] Patent Number: 4,929,847
[45] Date of Patent: May 29, 1990

[54] RAPID DETERMINATION OF SLUDGE CONTENT AND DEVICE THEREFOR

[75] Inventors: Seigo Yamazoe; Sadao Nakai; Yukimasa Fukui, all of Saitama, Japan

[73] Assignee: Cosmo Oil Co., Ltd., Tokyo, Japan

[21] Appl. No.: 348,742

[22] Filed: May 4, 1989

[30] Foreign Application Priority Data

May 9, 1988 [JP] Japan ............................. 63-110512
Nov. 1, 1988 [JP] Japan ............................. 63-274383

[51] Int. Cl.$^5$ ........................................... G01N 15/06
[52] U.S. Cl. .................................... 250/573; 356/436
[58] Field of Search ............... 250/226, 227, 573, 577; 356/436, 437, 440

[56] References Cited

U.S. PATENT DOCUMENTS

| | | | |
|---|---|---|---|
| 2,761,067 | 8/1956 | Troy, Jr. .............................. | 250/573 |
| 3,781,092 | 12/1973 | Sussman et al. ..................... | 250/227 |
| 3,790,156 | 6/1975 | Heigl et al. .......................... | 356/440 |
| 4,136,959 | 1/1979 | Honkawa et al. ................... | 356/436 |
| 4,544,840 | 10/1985 | Keller ................................... | 250/573 |
| 4,843,247 | 6/1989 | Yamazoe et al. ................... | 250/573 |

Primary Examiner—David C. Nelms
Assistant Examiner—Stephone B. Allen
Attorney, Agent, or Firm—Sughrue, Mion, Zinn, Macpeak & Seas

[57] ABSTRACT

A method for determining a sludge content in a heavy hydrocarbon oil and a device therefor are disclosed. The method comprises measuring absorbances of a heavy hydrocarbon oil sample, having an oil film thickness selected form a range of form about 0.01 to 5 mm, at two different wavelengths selected from the visible light region of from 500 to 1000 nm and determining a sludge content of the sample oil by comparing two measured absorbances according to the relationship between known sludge contents and absorbances at the two wavelengths. The device comprises a light source, a cell for a sample oil, a two-wavelength absorbance detector containing two interference filters and two light-current transducers, and a computing means for converting the current values obtained into a sludge content. The method and device provide a means for rapid and precise determination of sludge contents in heavy hydrocarbon oils.

10 Claims, 3 Drawing Sheets

RAPID DETERMINATION OF SLUDGE CONTENT AND DEVICE THEREFOR

FIELD OF THE INVENTION

This invention relates to a method for rapidly determining a sludge content in heavy hydrocarbon oils, such as desulfurization residue, hydrocracked oils, thermally cracked oil, long residue, short residue, liquefied coal oil, shale oil, tar and oil, etc., and to a device for automatically carrying out such a determination.

BACKGROUND OF THE INVENTION

Heavy hydrocarbon oils sometimes contain solid or semisolid substances called sludge. Sludge formation is frequently observed when residual oils produced under severe conditions from a desulfurization apparatus, a hydrocracking apparatus, a thermal cracking apparatus, a catalytic cracking apparatus, etc., or heavy hydrocarbon oil-based mixed oils of these residual oils are preserved under improper conditions. In particular, in the recent use of cracking residues as a base for fuel oils, generation of sludge has caused serious problems in terms of the practical use of the fuel oils. These problems include obstruction of a strainer and formation of a deposit in the tip of an oil burner. The stability of fuel oils has thus been a subject of global interest.

In order to prevent these problems, a technique of rapid and precise determination of the sludge content in heavy hydrocarbon oils must be established so that the stability of heavy hydrocarbon oils can be judged for quality control.

The cause of sludge formation is considered as follows. Heavy hydrocarbon oils generally contain high-molecular weight aromatic condensed polycyclic components called "asphaltene". Asphaltene generally adsorbs aromatic components of maltene having relatively high molecular weights so as to form stable micelles. Asphaltene is an insoluble matter formed upon addition of n-heptane to heavy hydrocarbon oils. Maltene is the component soluble in n-heptane. It is considered that the stable micelles of asphaltene in the form of a colloidal dispersion lose their balance upon undergoing admixture with other fuels, thermal influence, oxidation, and the like, i.e., the micelles agglomerate and flocculate, whereby the stability of the heavy hydrocarbon oils is deteriorated and a sludge is formed. The sludge is therefore a solid or semisolid substance formed by agglomeration of aromatic components having a high condensation degree that are present in the heavy hydrocarbon oils, without forming stable micelles. Sludge is different from asphaltene which is precipitated on addition of n-heptane to heavy hydrocarbon oils. Thus, the sludge possesses different properties form those of asphaltene.

Conventional test methods for evaluating the stability of heavy hydrocarbon oils include a xylene equivalent test method, a spot test, etc., but they are not applicable to determination of sludge content. Moreover, these methods involve complicated operations, and the results obtained lack precision.

Since there is no officially standardized method of sludge determination, a Shell hot filtration test method, SMS 2696-83, which is an internally specified standard of Shell Oil Co. (hereinafter referred to as the "Shell hot filtration method") has been commonly employed for sludge determination. The Shell hot filtration method comprises pouring a sample oil on a filter fitted to a strainer of a double jacket heating system heated to 100° C. so as to effect filtration under reduced pressure until no oily content is noted on the filter paper, washing the solid to semisolid substance collected on the filter with n-heptane, drying the collected substance for a given period of time, followed by weighing to obtain a dry sludge content, and determining a sludge concentration in the sample oil. However, this method, which is in the nature of a filter cake weighing method, involves complicated and troublesome operations, requires about 2 hours for obtaining the test results, and exhibits poor reproducibility. Besides, this method is unapplicable to those oils having high viscosities of 700 cSt or higher at 50° C. because of the extended time required for filtration.

In the light of the latest petroleum situation, developments and studies on the lightening of heavy hydrocarbon oils have been intensively continued. Under these circumstances, it has been desired to develop a technique for rapidly determining a sludge content of heavy hydrocarbon oils, an important parameter for evaluating the stability of heavy hydrocarbon oils and heavy hydrocarbon oil-based mixed oils, and a device for carrying out such a determination.

SUMMARY OF THE INVENTION

One object of this invention is to provide a method for determining a sludge content of heavy hydrocarbon oils more rapidly and for a winder range of concentration as compared with the conventionally proposed filter cake weighing method.

Another object of this invention is to provide a device for carrying out the above-described sludge determination.

It has now been found that the above objects of this invention can be accomplished by a technique combining a means for adjusting a sample oil so as to have a given oil film thickness and two-wavelength absorptiometry and by a device composed of a two-wavelength absorbance detector for determining a sludge content of heavy hydrocarbon oils, a movable sample stand connected to the detector for automatically feeding a cell containing a sample oil to a photometric part, and a microcomputer connected to the detector.

The present invention comprising the constructions stated above makes it possible to treat a variety of samples rapidly and precisely without involving much labor.

That is, the present invention relates to a method for determining a sludge content in a heavy hydrocarbon oil, which comprises the steps of:

(A) measuring absorbances of a heavy hydrocarbon oil sample having an oil film thickness of about 0.01 to 5 mm at two different wavelengths selected from the visible light region of from 500 to 1000 nm, and (B) determining a sludge content of the sample by comparing the two measured absorbances according to the relationship between known sludge contents and absorbances at the two wavelengths.

The present invention further relates to a device for determining a sludge content in a heavy hydrocarbon oils, which comprises a light source, a cell for a heavy hydrocarbon oil sample, wherein an oil film having a thickness of from about 0.01 to 5 mm is provided through which light from the light source is transmitted, a two-wavelength absorption detector composed of two interference filters each capable of transmitting the light rays having transmitted through the sample having different wavelengths selected from the range of from 500 to 1000 nm, and two light-current transducers each capable of converting the intensity of each of the transmitted light rays having two different wavelengths into an electrical current, and a computing means capable of converting the current values into a sludge content.

DETAILED DESCRIPTION OF THE INVENTION

The principle of the method of sludge determination according to the present invention is as follows.

(1) An adequate amount of a sample oil is collected in a cell and, after adjusting the thickness of the sample oil film to a predetermined value within a range of from about 0.01 to 5 mm, kept at a constant temperature. Light is transmitted through the sample, and optical densities (absorbances) of the sample oil at two different wavelengths having an appropriate wavelength difference therebetween within a range of from about 500 to 1000 nm are measured. The absorption spectrum of the sample oil in the visible wavelength region of from 500 to 1000 mn has no absorption maximum, showing a substantially linearly descending tendency as the wavelength becomes longer.

Figure 1:
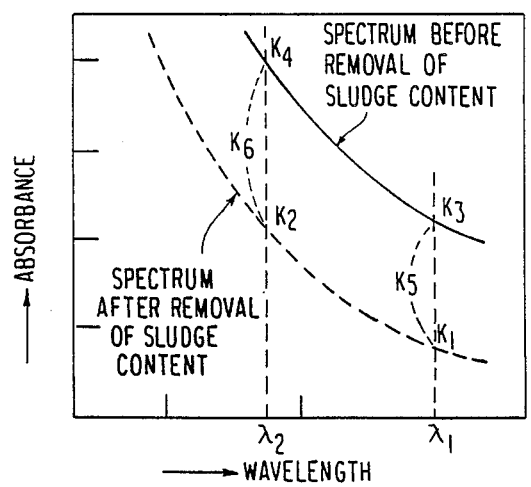
FIG. 1 is an absorption spectrum measured in the visible light region of both a sample oil and a sample oil from which sludge has been removed by filtration.

FIG. 1 is a model of an absorption spectrum of both the sample oil stated above and a sample oil prepared by removing sludge from the same sample oil by filtration or the like means (i.e., blank), in which the wavelength of light is plotted as the abscissa and the absorbance corresponding to a sample thickness of 1 mm as the ordinate. In FIG. 1, the solid line is an absorption spectrum of the sample oil before removal of sludge, and the dotted line is an absorption spectrum of the sample after removal of sludge. Irrespective of the kind of oils, such as desulfurization residue, hydrocracked oil, thermally cracked oil, long residue, short residue, and liquefied coal oil, the sludge particles to be determined have a particle size of about 5 μm or less with an almost uniform size distribution and transmit substantially no light having wavelengths between about 500 nm and about 1000 nm. Accordingly, the absorbance of the sample oil from which the sludge particles have been removed is lower than that of the sample oil before sludge removal by the absorbance corresponding to the sludge content of the sample oil before removal of sludge, and drops substantially linearly as the wavelength become longer. It has been confirmed through investigations on various heavy hydrocarbon oils that there is a first-order correlation between (i) a ratio of (a difference between absorbance $K_4$ of the sample oil before removal of sludge at wavelength $\lambda_2$ and absorbance $k_3$ of the same sample oil at wavelength $\lambda_1$) to absorbance $K_3$, i.e., $(K_4-K_3)\times 100/K_3$, (hereinafter referred to as the "rate of increase") and (ii) a ratio of absorbance $K_1$ of the sample oil after removal of sludge at wavelength $\lambda_1$ to absorbance $K_3$, i.e., $K_1\times 100/K_3$, (hereinafter referred to as the "blank rate") even if the kind or sludge content of oil changes.

Therefore, absorbance $K_1$ after sludge removal at analytical wavelength $\lambda_1$ can be obtained by measuring absorbances of a sample oil whose thickness has been adjusted within a range of from about 0.01 to 5 mm at two different wavelengths and by inserting the measured values in the correlation of (i) the rate of increase with (ii) the blank rate. Absorbance $K_5$ corresponding to the sludge content can then be obtained from a difference between $K_3$ and $K_1$.

Thus, a sludge content of a sample oil can be obtained from a calibration curve of a known sludge content per 100 g of a sample oil as determined by the Shell hot filtration method and absorbance $K_5$.

(2) Based on the above-described principle, the calculation of a sludge content can be appropriately modified. That is, the sludge content can also be obtained by utilizing a first-order correlation between an absorbance ratio $K_4/K_3$ and a ratio of sludge weight (g) in a sample oil to absorbance $K_3$, i.e., $g/K_3$. The sludge weight in the sample oil can be obtained by the Shell hot filtration method, too. Accordingly, once a relationship between the absorbance ratio $K_4/K_3$ and the ratio $g/K_3$ for a known sample is established, a sludge content in a sample oil can be obtained from a previously prepared calibration curve by simple measuring absorbances $K_3$ and $K_4$.

(3) In accordance with the above-described method of determination, determined values of about 50 kinds of heavy hydrocarbon oils having sludge contents between about 0.05 and 10% by weight correlate with the values as determined by the Shell hot filtration method with a coefficient of correlation of 0.99 or more. In addition, the coefficient of variation is 2% or less. This indicates excellent analytical precision (the analytical precision of the Shell hot filtration method is not specified in the nature of a filter cake weighing method). The time required for a cycle of analysis is about 5 minutes, which is markedly shorter than that required in the shell hot filtration method or any other test methods for evaluating the stability of fuel oils. The principle of the determination method according to the present invention is similar to the technique disclosed in JP-A-62-110135 corresponding to U.S. Pat. application Ser. No. 080,511 (the term "JP-A" as used herein means an "unexamined published Japanese patent application"). However, the method of this invention is characterized in that sludge contents in samples can be directly determined without requiring any pre-treatment of samples as involved in JP-A-62-110135, such as addition of a solvent to samples followed by stirring to precipitate an insoluble matter.

In carrying out the determination according to the present invention, a sample oil is adjusted so as to have a prescribed oil film thickness of within a range of from about 0.01 to 5 mm. This is achieved by adjusting the thickness of a cell in which a sample is put or adjusting the distance between a light source and a two-wavelength absorbance detector or the distance between (a) a light source and a two-wavelength absorbance detector set by the light source and (b) a reflector, which are put on a sample stand equipped with a sample heating means, by which the stand is heated, if desired, at about 40 to about 100° C., preferably about 60 to about 70° C. The oil thickness is adjusted within the above recited range in accordance with the kind of the oil under analysis so that measured absorbances may be not more than about 3, which assure high analytical precision.

If a sample oil contains a wax content, a precipitate of the wax content influences the analytical precision. It is therefore preferable to place a sample-containing cell on a stand equipped with a heating means. The heating means may be a heating element, e.g., a heater, buried inside or a warm water circulatory system. The heating temperature is usually from about 40 to 100° C., preferably from about 60 to 70° C. Temperatures lower than about 40° C. are insufficient for preventing precipitation of the wax content, and those higher than about 100° C. cause fluidization and agglomeration of the solid to semisolid sludge particles so as to change the particle size. This results in deterioration of the analytical precision.

Incident light emitted from a light source is transmitted through the sample oil film having a prescribed thickness. Absorbances of the sample oil at two different wavelengths within a range of from about 500 to 1000 nm with an appropriate difference therebetween are measured.

The intensity of each of the two transmitted light rays is converted into an electrical current value by means of a light-current transducer, which is then put into a computer having a prescribed program thereby to print out a sludge content in the sample oil. Whether the program of the computer is set to make a calculation based on $(K_4-K_3)\times 100/K_3$ or on $K_4/K_3$, the calculated values ought to be equal.

The absorbance measurement according to the two-wavelength absorptiometric detection can be carried out by transmitting the incident light through a sample oil in the cell and leading the transmitted light to a two-wavelength absorption detector where the absorbances at two wavelengths are measured. When more than one cell containing different sample oils is put on a stand which can be moved or turned under control so that each cell may be successively moved to the location of measurement, sludge contents of different sample oils can be continuously and efficiently measured.

The thickness adjustment of the sample oil film can be achieved either by using a specific cell hereinafter described or by controlling the distance between a light source dipped in or contacted with a sample oil and a two-wavelength absorbance detector or the distance between a light source and a two-wavelength absorbance detector set thereby and a reflector. Throughout the above-described determination, all of the processes can be controlled based on the computer program, thus greatly saving labor.

The cell for adjusting the thickness of a sample oil film is shown in Figs and composed of flat plate 11 made of colorless transparent glass or quartz, ring spacer 12 made of glass, quartz, a metal (e.g., lead, aluminum), or a plastic (e.g., Teflon), and grooved plate 13 made of colorless transparent glass or quartz. An adequate amount, e.g., from about 0.01 to 1 g, of a sample oil is placed on the center of grooved plate 13, and plate 11 is overlaid thereon with spacer 12 having a thickness selected from about 0.01 to 5 mm so that the measured absorbance would be 3 or less being interposed therebetween. The sample oil thus confined in the space surrounded by ring spacer 12, flat plate 11, and grooved plate 13 has a thickness corresponding to the thickness of the spacer 12. Even when the sample oil is fed in excess, the excess flows into the groove provided on the plate 13 without running out from between the plate 13 and the spacer 12, thereby adjusting the oil film thickness to correspond to the thickness of the spacer. The cell composed of the grooved plate 13, spacer 12, and flat plate 11 having contained therein the sample oil is placed on a stand heated to about 70° C. After the cells are heated to that temperature, the absorbances of the sample in each cell are measured at two different wavelengths selected from the range of from about 500 to 1000 nm with a wavelength difference of at least about 20 nm, preferably from about 30 to 100 nm, for example, at an analytical wavelength of 800 nm and at a control wavelength of 750 nm. If the difference between the two wavelengths selected is less than about 20 nm, the determination precision becomes poor.

The device for sludge determination according to the present invention is described below in detail.

One embodiment of the device comprises a stand on which a cell is placed, a light source fitted over one side of the stand, a passage for light to allow the light from the light source to pass through a sample oil contained in the cell and to reach a two-wavelength absorbance detector, two interference filters each capable of transmitting the light rays having transmitted through the sample oil having different wavelengths selected from the range of from about 500 to 1000 nm, a two-wavelength absorbance detector composed of two light-current tansducers each capable of converting the intensity of each of the two transmitted light rays into an electrical current, and a computing means capable of converting the electrical current values into a sludge content.

Another embodiment of the device comprises a light source which is dipped in or contacted with a sample oil, a means for precisely controlling the distance between the light source and a two-wavelength absorbance detector which is provided so as to face with the light source with a sample oil therebetween or the distance between a two-wavelength absorbance detector which is provided at the side of the light source and a reflector which is provided so as to face toward the light source with a sample oil therebetween, a two-wavelength absorbance detector composed of two interference filters each capable of transmitting the light rays having transmitted through the sample oil having different wavelengths selected from the range of from about 500 to 1000 nm and two light-current transducers each capable of converting the intensity of the each of the transmitted light rays having different wavelengths into an electrical current, and a computing means capable of converting the electrical current values into a sludge content.

The stand having cells thereon, which is heated to a prescribed temperature by means of a heating means, moves (turns) until a cell to be analyzed reaches a position of measurement, i.e., at the passage of light from the light source to the two-wavelength absorbance detector. Alternatively, the distance between the light source dipped in or contacted with the sample oil and the two-wavelength absorbance detector or the distance between the light source set by the side of the two-wavelength absorbance detector and the reflector is controlled to adjust the oil film thickness within a range of from about 0.01 to 5 mm. Light from the light source is transmitted through the sample oil film having the thus adjusted thickness. The transmitted light enters into the two-wavelength absorbance detector, where it is divided into two, each part of which is passed through each of the two interference filters being different in wavelength to select two light rays having appropriately different wavelengths within the range of from about 500 to 1000 nm, and the absorbance of the sample oil at each of the different wavelengths is measured.

The intensity of the light transmitted through each filter is converted into an electrical current by a light-current transducer, such as a phototube and a photocell, and the resulting current values are introduced into a computer having a specified program to perform an operation to print out the sludge content in the sample oil under analysis.

On completion of sludge determination through the above-described processes, the cell stand is again moved or turned under instructions from the computer to stop at a cell containing another sample oil at the above-described position of measurement. Through these procedures, one cycle of sludge determination completes.

Figure 4:
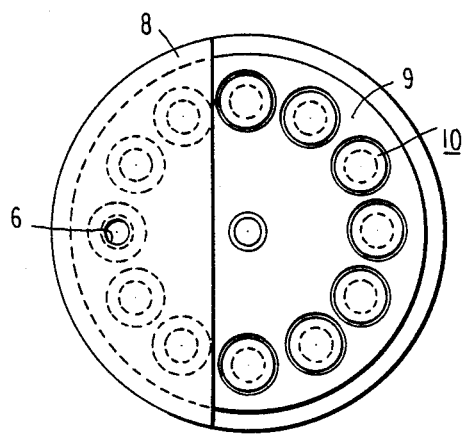
FIG. 4 is a plan view of a sample heating means and the sample stand of the automatic determination device of FIG. 2.
Figure 5:
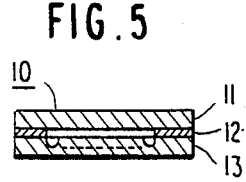
FIG. 5 is a cross-section of the cell of a sample oil.
Figure 2:
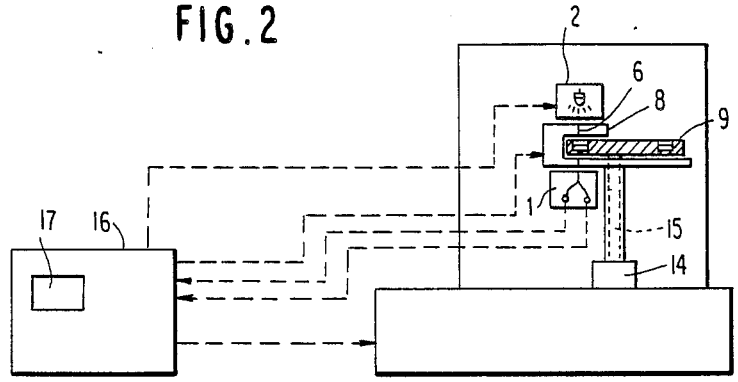
FIG. 2 is a block diagram illustrating an example of the automatic determination device according to the present invention.
Figure 3:
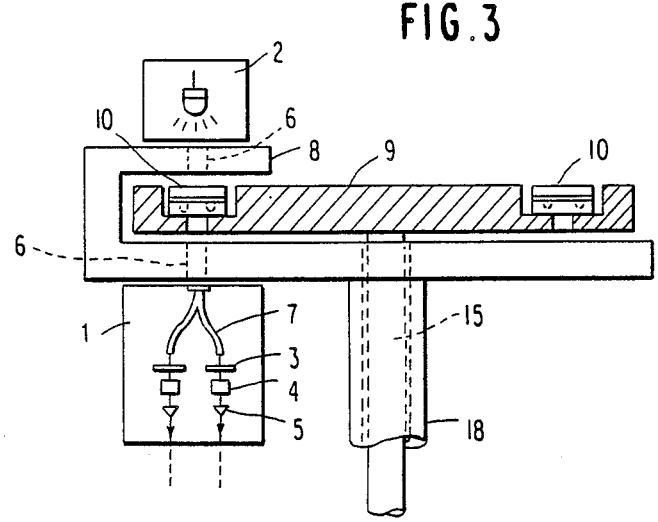
FIG. 3 is an enlarged view of the photometric part of the automatic determination device of FIG. 2.

FIG. 2 is a block diagram illustrating one embodiment of the device according to the present invention; FIG. 3 is an enlarged view of the main part thereof; FIG. 4 is an enlarged plan view of the cell stand used therein; FIG. 5 is a cross-section of the cell; and FIGS. 6-(a), (b), and (c) are elements constituting the cell, in which (a) is a flat plate, (b) is a spacer, and (c) is a grooved plate.

The determination device according to the embodiment of FIG. 2 comprises turntable 9 (cell stand) having two or more recess wells for cells to be held at the peripheral portion thereof, light source 2, two-wavelength absorbance detector 1, the light source 2 and the two-wavelength absorbance detector 1 being provided so as to face each other with one of the wells at the periphery of the turntable being interposed therebetween, driving motor 14 and rotating axis 15 driven by the motor 14 which is capable of turning turntable 9 at a prescribed angle, and microcomputer 16 capable of controlling the motor 14 to intermittently drive the rotating axis 15 and converting electrical current values from the two-wavelength absorbance detector 1 into a sludge content.

In FIG. 3, the two-wavelength absorbance detector 1 is composed of passage 6 for leading light emitted from the light source 2 (e.g., a tungsten lamp), optical fiber bundles 7 for dividing the light transmitted through the sample oil film into two ways, interference filters 3 (e.g., 750 nm and 800 nm), light-current transducers 4 (e.g., phototubes or solar cells), and amplifiers 5. The optical fiber bundle 7 used in this embodiment for dividing the transmitted light into two may be replaced with a sector mirror.

The recess wells in which each of cell 10 is to be held are provided at the peripheral portion of the turntable 9 at regular intervals. For assuring precision in sludge determination of sample oils containing a wax content, heating means 8 is provided in the vicinity of the passageway of the cell 10 mounted on the turntable 9. As shown in FIGS. 2 and 3, the heating means 8 is fitted to the fringe of fixed outer cylinder 18 through which the rotating axis 15 is inserted. The heating means 8 contains therein a heating element, e.g., a heater, and is controlled at a given temperature by the instructions from the microcomputer 15 thereby heating the cell 10 to a prescribed temperature by the time when the cell reaches the light passage 6 at the latest. The turntable 9 is made to turn by the connection to the driving motor 14 and the rotating axis 15. The start and stop of movement of the turntable 9 are under control of instructions sent from the microcomputer 16 to the driving motor 14.

Figure 6A:
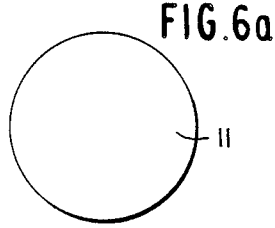
FIGS. 6-(a), (b), and (c) each show a plan view of each part constituting the cell of FIG. 5.
Figure 6B:
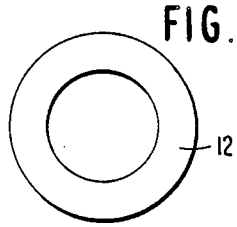
Figure 6C:
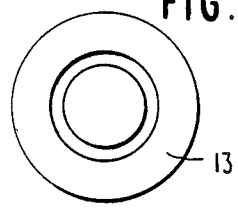

As shown in FIGS. 5 and 6, the cell 10 is composed of flat plate 11 having a disc form, spacer 12, and grooved plate 13. The thickness of the spacer 12 decides the film thickness of a sample oil. Returning to FIG. 2 and 3, the light transmitted through a sample oil film in the cell 10 is divided into two light rays having different wavelengths in the two-wavelength absorbance detector 1. The intensity of each light ray is converted into the respective electrical current, and the output current is put into the microcomputer 16, where an operation is performed according to a previously set program to convert the current values into a sludge content of the sample oil, which is then printed out by printer 17.

More specifically, the driving motor 14 starts to drive the rotating axis 15 on receipt of signals from the microcomputer 16, whereby the cell stand is turned around the axis 15. When one of the cells 10 comes into the light passage 6, the driving motor 14 stops. While the cell 10 being held at that position, visible light emitted from the light source 2 is transmitted through the passage 6 in the vinicity of the sample heating means 8 and through the sample oil film in the cell 10. The light is partly absorbed in the oil film and partly reaches the two-wavelength absorbance detector 1. The transmitted light is then divided into two by means of the optical fiber bundles 7, and each of which reaches each of the interference filters 3, where the intensity of the respective light is converted into an electrical current by means of the respective light-current transducer (e.g., a phototube), amplified by the amplifier 5, and then introduced in the microcomputer 16.

In the microcomputer 16, the current input is converted into transmittance T (ratio of transmitted light I/incident light $I_0$), which is then converted into absorbance K ($\log_{10} 1/T$). The resulting absorbance values are applied to a correlation of the rate of increase-blank rate and a calibration curve of the absorbance difference $K_3-K_1$ vs. sludge content that has previously been put in the computer to calculate a sludge content, which is then put in the printer 17. On completion of the output, signals are issued from the microcomputer 16 to start the driving motor 14, whereby the turntable again starts to turn to set the next cell 10 on the location of measurement, and the same operations as described above are automatically repeated. In the embodiment of the determination device, various modifications are possible. For example, the turning movement of the cell stand 9 may be replaced with linear movement. Further, the light pass may be changed if desired by providing mirrors or prisms in the light passage 6. Furthermore, two light rays having different wavelengths may be previously selected before transmission through the sample oil, and each of which is received by the respective light-current transducer. The purposes and effects aimed in the present invention can be achieved by any of these modifications.

Figure 7:
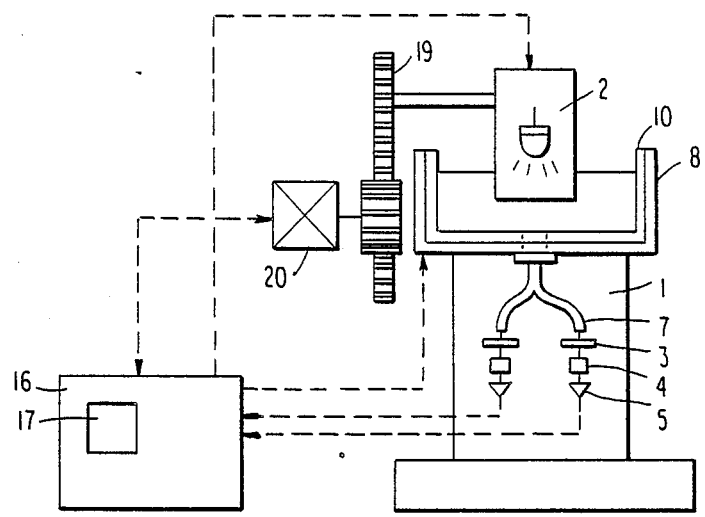
FIGS. 7 and 8 each is a block diagram illustrating another example of the automatic determination device according to the present invention.
Figure 8:
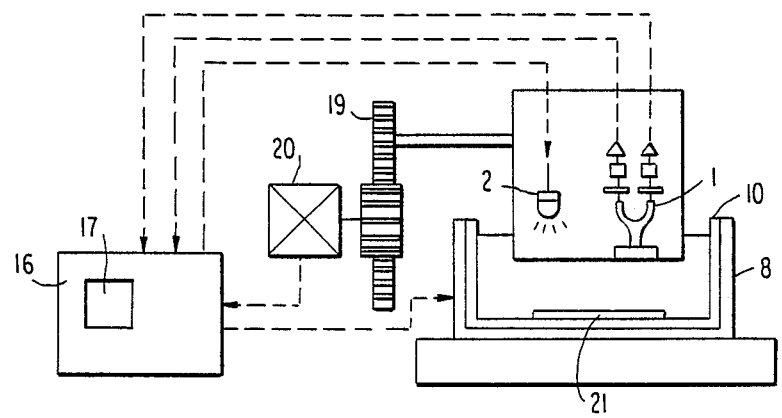

FIG. 7 and 8 each illustrates another embodiment of the determination device according to the present invention, in which an arbitrary oil film thickness can be obtained without using the aforesaid spacer having a prescribed thickness. The device according to this embodiment has rack-and-pinion gear 19 and computer-controlled stepping motor 20 which are capable of minutely moving light source 2 dipped in or contacted with a sample oil or a unit containing light source 2 and two-wavelength absorbance detector 1 on the same side of the sample oil which is dipped in or contacted with a sample oil. In short, when the sample oil is sandwiched between the light source 2 and the two-wavelength absorbance detector 1 as shown in FIG. 7, the prescribed oil film thickness can be obtained by minutely moving either one of them. When the sample oil is sandwiched between a unit containing light source 2 and two-wavelength absorbance detector 1 on the same side and reflector 21 provided on the opposite side of the sample as shown in FIG. 8, the prescribed oil film thickness can be obtained by minutely moving either one of said unit and said reflector.

In FIG. 7 wherein light source 2 dipped in or contacted with a sample oil and two-wavelength absorbance detector 1 are facing toward each other with the sample oil being sandwiched therebetween, stepping motor 20 is controlled by signals from microcomputer 16 to move the light source 2 with fine up-and-down strokes within the sample oil via rack-and-pinion gear 19 to thereby obtain a proper oil film thickness. As a matter of course, it is possible to adjust the oil film thickness by connecting the rack-and-pinion gear 19 to the two-wavelength absorbance detector and vertically moving the two-wavelength absorbance detector 1 together with the sample-containing cell 10. Further, the light emitted from the light source 2 may be led into the sample oil via optical fibers, and the light transmitted through the sample oil may be led into the two-wavelength absorbance detector 1 via optical fibers connected thereto so that the ends of the two optical fiber bundles face each other with the sample oil therebetween. In this case, either one or both of the two optical fiber bundles is or are moved by means of the stepping motor 20 to control the distance between the two optical fiber bundles thereby to obtain a proper oil film thickness. Furthermore, the oil film thickness may be adjusted while either one of the light source 2 and the two-wavelength absorbance detector 1 is fixed to the device without using optical fibers. The device of the invention thus includes a variety of modification.

In FIG. 8 wherein light source 2 and two-wavelength absorbance detector 1 are provided on the same side with respect to a sample oil, the light emitted from the light source 2 is transmitted through the sample oil and reflected on reflector 21 provided in the sample oil, and the reflected light is received by the two-wavelength absorbance detector 1. The thickness of the oil film sandwiched between the unit containing the light source 2 and the two-wavelength absorbance detector 1 and the reflector 21 can be properly adjusted by controlling the distance between them by means of the stepping motor 20. With respect the fitting position of each of the light source 2, two-wavelength absorbance detector 1, and reflector 21 or the moving relationship among them, various modifications as described for the embodiment of FIG. 7 are also applicable to this embodiment.

As shown in FIGS. 7 and 8, the oil film thickness adjustment can be achieved by controlling the distance between light source 2 which is dipped in or contacted with a sample oil and two-wavelength absorbance detector 1 or the distance between light source 2 and two-wavelength absorbance detector 1 being set by light source 2 and reflector 21 which is provided on the bottom of cell 10, facing towards the light source 2 and the detector 1. Either one of the light source 2 and the two-wavelength absorbance detector, or either one of the unit containing the light source 2 and the two-wavelength absorbance detector 1 and the reflector 21 is vertically moved by moving rack-and-pinion gear 19 driven by stepping motor 20 under control of microcomputer 16 so as to adjust the above-described distance within a range of from about 0.05 to 5 mm. On confirmation that the aforesaid distance is obtained by pulse signals from the stepping motor 20, absorbances of the light transmitted through the sample oil at the two different wavelengths are measured.

According to the above-described technique, the oil film thickness through with the light from the light source is transmitted can be arbitrarily set by micromillimeters according to the kind of the oil so that the light can transmit through the sample. The present invention will now be illustrated in greater detail with reference to the following Examples, but the present invention is not to be construed as being limited thereto.

EXAMPLES

Referring to FIG. 1, when, for example, the absorbance of a sample oil converted to an oil film thickness of 1 mm at an analytical wavelength $\lambda_1$ of 800 nm ($K_3$) and that at a control wavelength $\lambda_2$ of 750 nm ($K_4$) are found to be 8.79 and 10.1, respectively, then the rate of increase, $(K_4-K_3) \times 100/K_3$, is 14.9. From the correlation between the rate of increase and the blank rate, one may obtain a blank rate of 28.3. It follows that $K_1$ (absorbance of the sample oil after sludge removal at the analytical wavelength of 800 nm)=2.49. Accordingly, $K_5$ (absorbance of sludge)=$K_3-K_1$ =6.30. The dry weight (g) and concentration (wt %) of sludge in the sample oil can be obtained from a calibration curve of absorbance $K_5$ and dry sludge weight (g) per 100 g of a sample oil.

Table 1 below shows the results of determinations of sludge contents in various heavy hydrocarbon oils in accordance with the method of the present invention in comparison with the results obtained by the Shell hot filtration method. Because the Shell hot filtration method could not be applied to sample oil Nos. 8 and 9 as they were due to their high viscosities, these samples were appropriately diluted with decalin, and the measured values were converted accordingly.

TABLE 1

| Sample Oil | Sludge Content (wt %) | |
|---|---|---|
| | Shell Hot Filtration Method | Method of Invention |
| (1) Hydrocracked oil-1 | 0.10 | 0.17 |
| (2) Hydrocracked oil-2 | 0.49 | 0.46 |
| (3) Hydrocracked oil-3 | 0.63 | 0.62 |
| (4) Hydrocracked oil-4 | 0.73 | 0.77 |
| (5) Direct desulfurization residue-1 | 2.49 | 2.43 |
| (6) Direct desulfurization residue-2[*1] | 2.62 | 2.77 |
| (7) (3) + (5) (1:1)[*2] | 1.93 | 1.98 |
| (8) Thermally cracked oil-1[*3] | 0.0 | 0.0 |

TABLE 1-continued

| Sample Oil | Sludge Content (wt %) | |
|---|---|---|
| | Shell Hot Filtration Method | Method of Invention |
| (9) Thermally cracked oil-2*4 | 0.99 | 1.19 |

Note:
*1Prepared by preserving Sample No. 5 at 60° C. for 7 days under atmospheric pressure.
*2Prepared by preserving a 1:1 (by volume) mixture of Sample Nos. 3 and 5 at 60° C. for 7 days under atmospheric pressure.
*3Cracking rate: 13%; Viscosity: 13500 cSt (50° C.)
*4Cracking rate: 36%; Viscosity: 5700 cSt (50° C.)

Table 2 below demostrates the determination precision of the method according to the present invention, giving measured values obtained through 6 measurements on each of Sample Nos. 3 and 5 of Table 1, and the mean, standard deviation, and coefficient of variation thereof. The coefficient of variation for a set of 6 measurements was obtained from the following equation:

$$\text{Coefficient of Variation (\%)} = \frac{\text{Standard Deviation Expressed in Square Root of Unbiased Variance}}{\text{Mean}} \times 100$$

TABLE 2

| | Hydrocraked Oil-3 | Direct Desulfurization Residue-1 |
|---|---|---|
| Measured Value: | | |
| Run No. 1 | 0.62 | 2.43 |
| Run No. 2 | 0.62 | 2.40 |
| Run No. 3 | 0.62 | 2.46 |
| Run No. 4 | 0.62 | 2.46 |
| Run No. 5 | 0.62 | 2.40 |
| Run No. 6 | 0.62 | 2.43 |
| Mean | 0.62 | 2.43 |
| Standard Deviation | 0.0 | 0.026 |
| Coefficient of Variation (%) | 0.0 | 1.21 |

As described above, the conventional methods and devices for determining a sludge content in heavy hydrocarbon oils suffer from various disadvantages, such as long periods of time required for sludge determination per sample, complicated operations and much labor involved, incapability of determining sludge contents of high viscosity heavy hydrocarbon oils, and poor analytical precision in some cases. On the other hand, the present invention provides a method and a device for determining a sludge content in heavy hydrocarbon oils by which a large number of samples can be automatically analyzed with high precision requiring a greatly reduced time per sample and relatively light labor.

While the invention has been described in detail and with reference to specific embodiments thereof, it will be apparent to one skilled in the art that various changes and modifications can be made therein without departing from the spirit and scope thereof.

What is claimed is:

1. A method for determining a sludge content in a heavy hydrocarbon oil, which comprises the steps of:
   (A) measuring absorbances of a heavy hydrocarbon oil sample having an oil film thickness of from about 0.01 to 5 mm at two different wavelengths selected from the visible light region of from 500 to 1000 nm; and
   (B) determining a sludge content of the sample by comparing the two measured absorbances according to the relationship between known sludge contents and absorbances at the two wavelength.

2. The method as claimed in claim 1, wherein said two wavelengths selected are different by at least 20 nm.

3. A device for determining a sludge content in a heavy hydrocarbon oil, which comprises a light source, a cell containing a heavy hydrocarbon oil sample, wherein an oil film having a thickness of from about 0.01 to 5 mm is provided through which light from the light source is transmitted, a two-wavelength absorption detector composed of two interference filters each capable of transmitting the light rays having transmitted through the sample having different wavelengths selected from the range of from 500 to 1000 nm and two light-current transducers each capable of converting the intensity of each of the two transmitted light rays having different wavelengths into an electrical current, and a computing means capable of converting the current values into a sludge content.

4. The device as claimed in claim 3, wherein said different wavelengths selected are different by at least 20 nm.

5. A device for determining a sludge content in a heavy hydrocarbon oil which comprises a stand on which a cell is placed, a light source fitted over one side of the stand, a passage for light to allow the light from the light source to pass through a sample oil contained in the cell and to reach a two-wavelength absorbance detector, a two-wavelength absorbance detector composed of two interference filters each capable of transmitting the light rays having transmitted through the sample oil having different wavelengths selected from the range of from about 500 to 1000 nm and two light-current tansducers each capable of converting the intensity of each of the two transmitted light rays into an electrical current, and a computing means capable of converting the electrical current values into a sludge content.

6. The device as claimed in claim 5, wherein said different wavelengths selected are different by at least 20 nm.

7. The device as claimed in claim 5, wherein said cell is composed of a transparent flat plate, a spacer having a prescribed thickness, and a transparent plate having a groove, and said device further comprises a means for moving the stand in such a manner that another cell is set at a location of determination every time a determination on a sample contained in one cell has been completed.

8. The device as claimed in claim 7, wherein said flat plate is made of transparent colorless glass or quartz, and said spacer is made of glass, quartz, a metal, or a plastic.

9. A device for determining a sludge content in a heavy hydrocarbon oil, which comprises a light source which is dipped in or contacted with a sample oil, a means for minutely adjusting the distance between said light source and a two-wavelength absorbance detector which is provided so as to face with said light source with a sample oil being sandwiched therebetween or the distance between a two-wavelength absorbance detector which is provided at the said of said light source and a reflector which is provided so as to face toward said light source with a sample oil being sandwiched therebetween, a two-wavelength absorption detector composed of two interference filters each capable of transmitting the light rays having transmitted through the sample oil having different wavelengths selected from the range of from about 500 to 1000 nm and two light-current transducers each capable of converting the intensity of the each of the transmitted light rays having different wavelengths into an electrical current, and a computing means capable of converting the electrical current values into a sludge content.

10. The device as claimed in claim 9, wherein said different wavelengths selected are different by least 20 nm.

* * * * *